United States Patent
Brennan

(10) Patent No.: US 10,751,114 B2
(45) Date of Patent: Aug. 25, 2020

(54) MANUFACTURING ELECTROSURGICAL INSTRUMENTS

(71) Applicant: Gyrus Medical Limited, St. Mellons, Cardiff (GB)

(72) Inventor: Neill Tomás Brennan, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 112 days.

(21) Appl. No.: 15/615,445

(22) Filed: Jun. 6, 2017

(65) Prior Publication Data

US 2017/0348045 A1    Dec. 7, 2017

(30) Foreign Application Priority Data

Jun. 7, 2016   (GB) .................................. 1609915.2

(51) Int. Cl.
| | | |
|---|---|---|
| *A61B 18/14* | (2006.01) | |
| *A61B 17/29* | (2006.01) | |
| *A61B 90/00* | (2016.01) | |
| *A61B 17/00* | (2006.01) | |
| *A61B 18/00* | (2006.01) | |

(52) U.S. Cl.
CPC .......... *A61B 18/1445* (2013.01); *A61B 17/29* (2013.01); *A61B 2017/00526* (2013.01); *A61B 2017/2936* (2013.01); *A61B 2017/2947* (2013.01); *A61B 2018/0063* (2013.01); *A61B 2090/034* (2016.02)

(58) Field of Classification Search
CPC ...... A61B 18/1445; A61B 2017/00526; A61B 2017/2936; A61B 2017/2947; A61B 17/2816; A61B 2017/2825
See application file for complete search history.

(56) References Cited

U.S. PATENT DOCUMENTS

| | | | | |
|---|---|---|---|---|
| 1,329,827 | A * | 2/1920 | Crittall | E05D 11/0009 29/11 |
| 2011/0082457 | A1* | 4/2011 | Kerr | A61B 18/1445 606/48 |
| 2011/0301592 | A1* | 12/2011 | Kerr | A61B 17/29 606/41 |
| 2012/0259331 | A1 | 10/2012 | Garrison | |
| 2013/0138101 | A1* | 5/2013 | Kerr | A61B 18/1442 606/45 |

OTHER PUBLICATIONS

Intellectual Property Office, Patents Act 1977: Search Report under Section 17(5) for United Kingdom Patent Application No. GB 1609915.2, dated Nov. 29, 2016 (3 pages).

* cited by examiner

*Primary Examiner* — Christopher M Koehler
*Assistant Examiner* — Kyle A Cook
(74) *Attorney, Agent, or Firm* — Honigman LLP; Matthew H. Szalach; Jonathan P. O'Brien

(57) ABSTRACT

A pair of jaw members for an electrosurgical instrument is manufactured by providing first and second jaw members (2 & 3), each jaw member including a planar sealing surface (5 & 7). The jaw members are assembled with the first and second jaw members in a required orientation such that the planar sealing surface (5) of the first jaw member (2) is at a predetermined orientation with respect to the sealing surface (7) of the second jaw member (3). The first and second jaw members are held in the required orientation, and pivot holes (11 & 12) are formed in the first and second jaw members while they are held in the required orientation. When a pivot pin is inserted through the pivot holes in the first and second jaw members, the first and second jaw members are assembled into a pair of jaws.

11 Claims, 3 Drawing Sheets

MANUFACTURING ELECTROSURGICAL INSTRUMENTS

CROSS-REFERENCE TO RELATED APPLICATIONS

This application claims the benefit of United Kingdom Patent Application Serial No. 1609915.2, filed Jun. 7, 2016, the entire contents of which are hereby incorporated by reference.

TECHNICAL FIELD

Embodiments of this invention relate to a method for manufacturing a pair of jaw members for an electrosurgical instrument, particularly a forceps instrument for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to manufacture jaw members for electrosurgical instruments by an overmoulding process, in which components are assembled into a mould and flowable material is introduced into the mould to surround the components and form the completed jaw member. U.S. Pat. Nos. 7,150,097 & 7,922,953 are examples of such manufacturing methods. However, unless the manufacturing tolerances for the jaws are strictly controlled, there is a chance that when the jaws are assembled together to form a pair of jaws, the tissue-contacting surface on one jaw may not be exactly in the required orientation with respect to the tissue-contacting surface on the other jaw.

SUMMARY OF THE INVENTION

Embodiments of the present invention attempt to avoid the above problem.

Accordingly, a method for manufacturing a pair of jaws for an electrosurgical instrument, comprises the steps of:

manufacturing first and second jaw members, each jaw member including a planar sealing surface, assembling the first and second jaw members in a required orientation such that the planar sealing surface of the first jaw member is at a predetermined orientation with respect to the sealing surface of the second jaw member, holding the first and second jaw members in the required orientation, forming a pivot hole in the first and second jaw members while they are held in the required orientation, and inserting a pivot pin through the pivot hole in the first and second jaw members to assemble the first and second jaw members into a pair of jaws.

By assembling the jaws into a required orientation before forming the pivot hole in both jaw members, it ensures that when the jaws are assembled with the pivot pin through the pivot holes, the jaw members will lie with respect to one another in the aforesaid required orientation. Preferably, the required orientation is such that the planar sealing surface of the first jaw member is parallel to the planar sealing surface of the second jaw member.

Typically, the pivot hole is formed in the first and second jaw members in a single operation, with the forming member passing through both jaw members as they are held one against the other. The step of forming the pivot hole preferably comprises drilling through the first and second jaw members with a drill bit. To maintain the jaw members in their required orientation, they are typically clamped together while the drilling is being carried out. In this arrangement, the formed pivot holes are of a diameter only slightly larger than the pivot pin, such that the pin can pass through the pivot holes, but with limited clearance such that the slack does not allow any significant variation in the orientation of one jaw member with respect to the other.

According to an alternative arrangement, the method includes the initial steps of forming an initial hole in the first and second jaw members before the assembly step, and filling the holes with a softer material before assembling the first and second jaw members. By "softer material", this material is relatively soft as compared with the material from which the remainder of the jaw members, typically stainless steel, is formed. According to this arrangement, the step of forming the pivot hole in the first and second jaw members while they are held in the required orientation comprises forming the hole through the softer material. Typically, the diameter of the pivot hole is less than the diameter of the initial hole in each of the first and second jaw members. In this way, a relatively large hole is initially formed in the jaw members, these holes are filled with the softer material, and the final pivot hole is then formed through the softer material when the jaw members are held in their required orientation. This means that the drilling, or other means of hole formation, is carried out through the softer material rather than through the metallic material of the jaw members themselves. Thus, the hole formation during the time that the jaw members are clamped together is made easier. Typically, this softer material is a polymeric material, such as polypropylene.

Embodiments of the invention further reside in a method of manufacturing a pair of jaws for an electrosurgical instrument, comprising the steps of:

manufacturing first and second jaw members, each jaw member including a planar sealing surface, and an initial pivot hole, filling the initial pivot hole in each of the first and second jaw members with a softer material, assembling the first and second jaw members in a required orientation such that the planar sealing surface of the first jaw member is at a predetermined orientation with respect to the sealing surface of the second jaw member, holding the first and second jaw members in the required orientation, forming a final pivot hole in the softer material while the first and second jaw members are held in the required orientation, and inserting a pivot pin through the final pivot hole in the first and second jaw members to assemble the first and second jaw members into a pair of jaws.

As described previously, the diameter of the final pivot hole is typically less than the diameter of the initial pivot hole in each of the first and second jaw members. As before, the softer material is typically a polymeric material.

DESCRIPTION OF THE DRAWINGS

Embodiments of the invention will now be further described, by way of example only, with reference to the accompanying drawings, in which.

DESCRIPTION OF THE EMBODIMENTS

Figure 1:
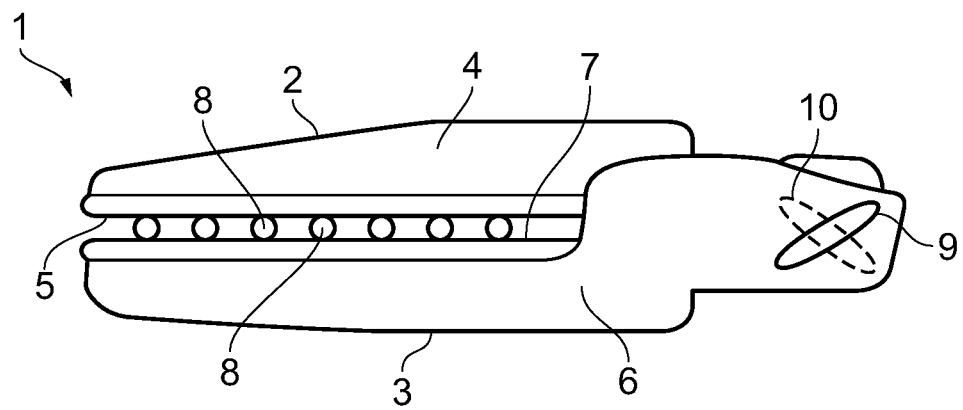
FIG. 1 is a schematic side view of a pair of jaws as part of a manufacturing method according to an embodiment of the present invention.

Referring to FIG. 1, an end effector shown generally at 1 comprises an upper jaw 2 and a lower jaw 3. Upper jaw 2 has a jaw body 4 and a substantially planar tissue sealing surface 5, while lower jaw 3 has a jaw body 6 and a corresponding planar tissue sealing surface 7. The sealing surfaces 5 & 7 are substantially parallel one to the other, and are separated by a plurality of stop members 8 located on one or both of the jaws.

Lower jaw body 6 is provided with an angled cam slot 9, while upper jaw body 6 has a corresponding oppositely angled cam slot 10, shown in dotted line detail. The jaws 2 & 3 are shown in FIG. 1 located together in a desired orientation with the sealing surfaces 5 & 7 parallel to one another, but the jaws are not at this stage connected to each other.

Figure 2:
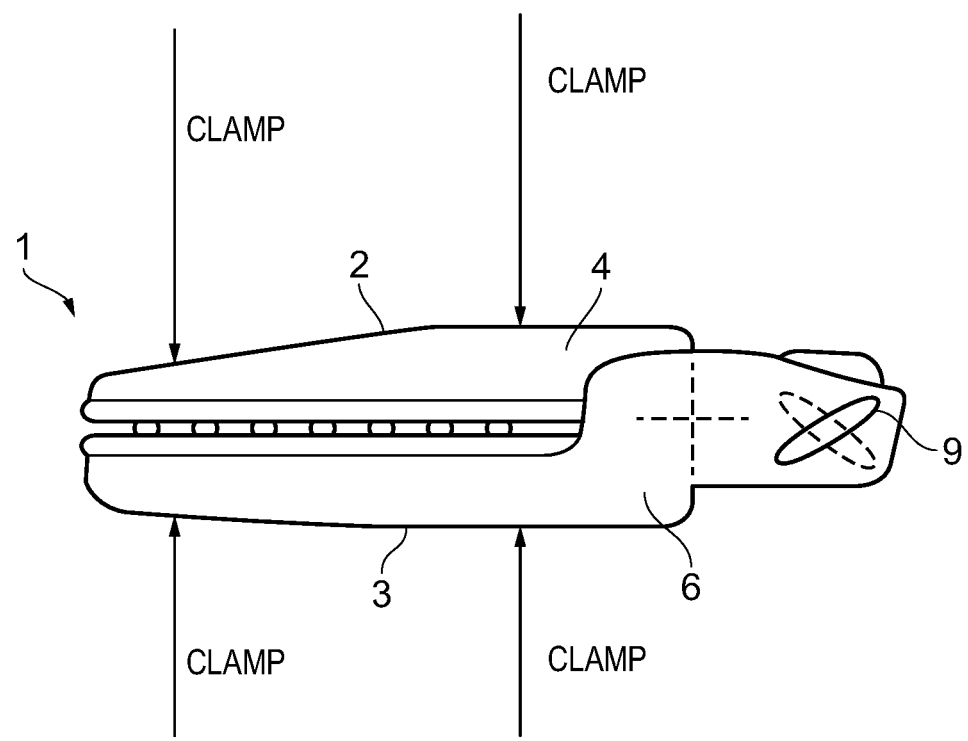
FIG. 2 is a side view of the jaws of FIG. 1 shown in a subsequent manufacturing step.
Figure 3:
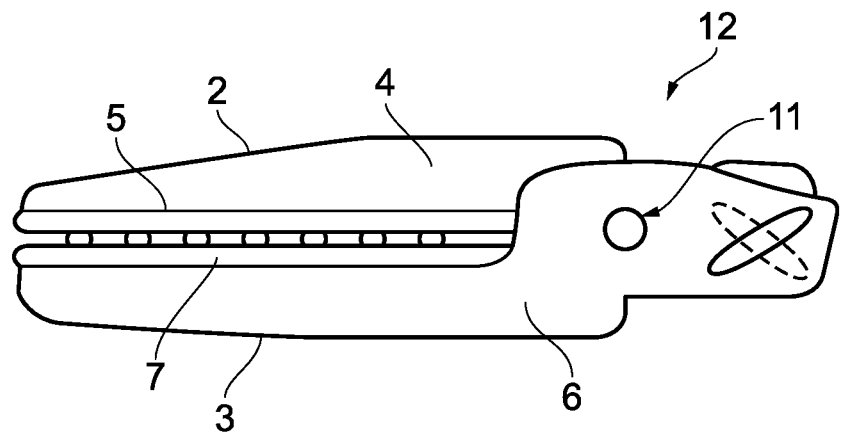
FIG. 3 is a side view of the jaws of FIGS. 1 & 2 shown in a further manufacturing step.

The jaws 2 & 3 are shown in FIG. 2 clamped in position, with clamps (not shown) engaging the jaw bodies 4 & 6 to hold them in the desired position. While clamped in position, a drill bit (not shown) drills a pivot hole 11 in jaw body 6, as shown in FIG. 3. The drill bit continues through jaw body 6 to drill a corresponding pivot hole 12 (though not directly visible in FIG. 3 as behind hole 11) in the jaw body 4. Pivot holes 11 & 12 are aligned such that when a pivot pin (not shown) is inserted through holes 11 & 12 the jaws 2 & 3 are assembled in their desired orientation with the sealing surfaces 5 & 7 parallel to one another.

Figure 4:
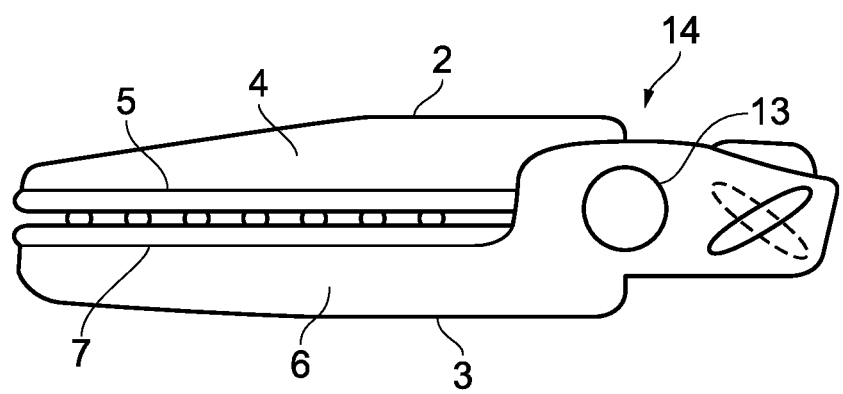
FIG. 4 is a side view of a pair of jaws as part of an alternative embodiment of manufacturing method according to the present invention.
Figure 5:
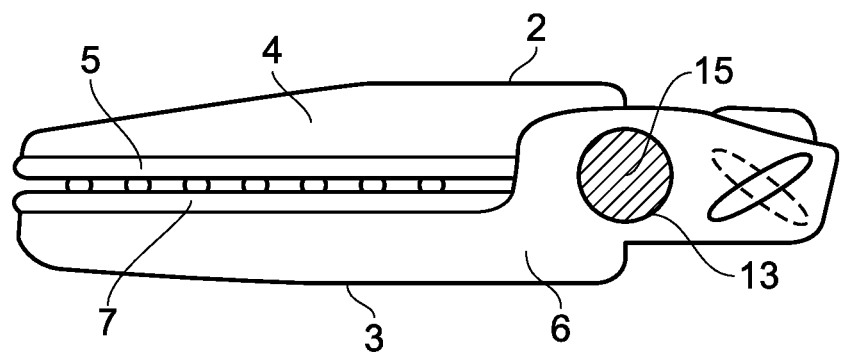
FIG. 5 is a side view of the jaws of FIG. 4 shown in a subsequent manufacturing step.
Figure 6:
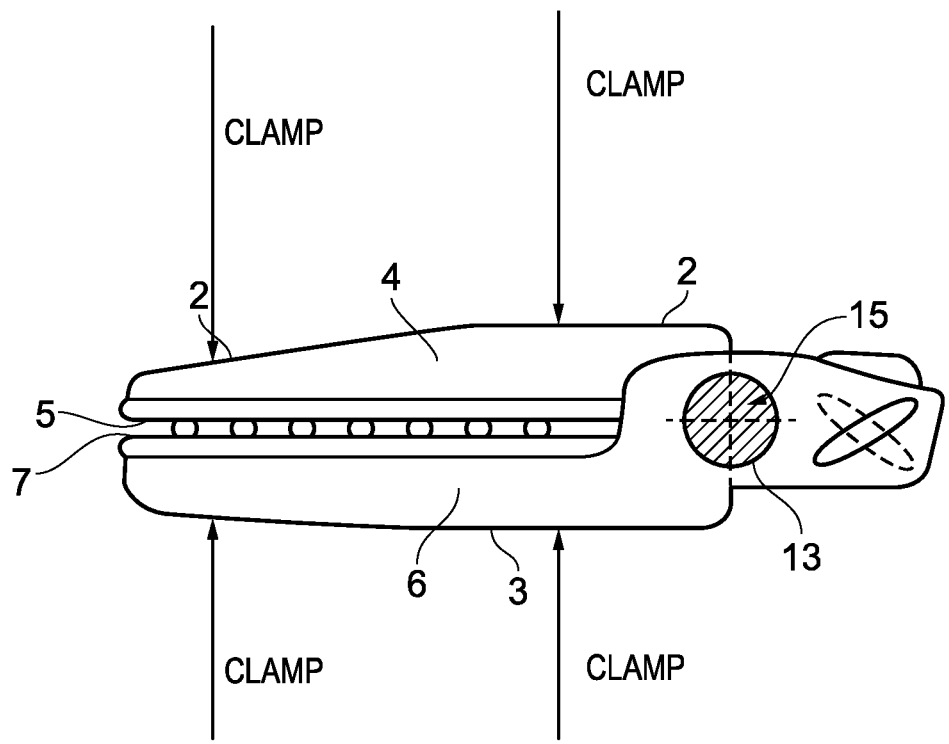
FIG. 6 is a side view of the jaws of FIGS. 4 & 5 shown in a further manufacturing step.
Figure 7:
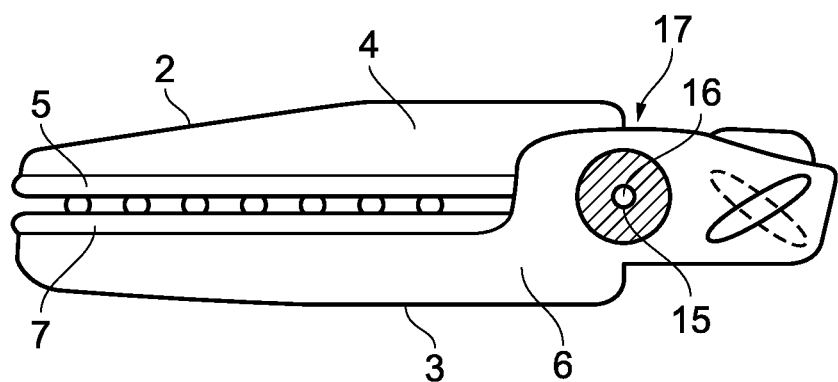
FIG. 7 is a side view of the jaws of FIGS. 4 to 6 shown in a subsequent manufacturing step.

FIG. 4 shows an alternative arrangement in which the jaws 2 & 3 are shown as before, with sealing surfaces 5 & 7 shown parallel one to another. The jaws of FIG. 4 are different from those of FIG. 1 in that they have been pre-drilled with initial large diameter holes 13 & 14. The jaws 2 & 3 are then placed into moulds and injection moulded such that the holes 13 & 14 are filled with a polymeric material to form polypropylene inserts 15, as shown in FIG. 5. Once the polypropylene material of the inserts 15 has hardened, the jaws are clamped in position as before, as shown in FIG. 6. While clamped in position, a drill bit (not shown) drills a pivot hole 16 through the polypropylene insert 15 in the lower jaw body 6, as shown in FIG. 7. The drill bit then continues through jaw body 6 to drill a corresponding pivot hole 17 (again not directly visible in FIG. 7 as behind hole 16) through the insert 15 in the jaw body 4. As the drill bit is drilling through polymeric material rather than through the metallic jaw bodies, the process is easier and with less vibration. Once again, pivot holes 16 & 17 are aligned such that when a pivot pin (not shown) is inserted through holes 16 & 17 the jaws 2 & 3 are assembled in their desired orientation with the sealing surfaces 5 & 7 parallel to one another.

Those skilled in the art will appreciate that modifications to the above can be made without departing from the scope of the present invention, and that alternative configurations of components can be employed. For example, although the desired orientation of the sealing surfaces 5 & 7 in the illustrated embodiments is with the sealing surfaces parallel to one another, this may not necessarily be the case. There may be circumstances where a desired orientation is with the sealing surfaces not parallel, but with the jaws 2 & 3 either "toed-in" (such that the distance between the sealing surfaces is greater towards the rear of the jaws as compared with the front), or "toed-out" (such that the distance between the sealing surfaces is greater towards the front of the jaws as compared with the rear). The key element is the formation of the pivot holes with the jaws already in their desired orientation, as opposed to pre-forming the pivot holes and then assembling the jaws.

The invention claimed is:

1. A method of manufacturing a pair of jaws for an electrosurgical instrument, comprising the steps of:
    manufacturing first and second metallic jaw members, each metallic jaw member including a planar sealing surface,
    assembling the first and second metallic jaw members in a required orientation such that the planar sealing surface of the first metallic jaw member is at a predetermined orientation with respect to the sealing surface of the second metallic jaw member,
    holding the first and second metallic jaw members in the required orientation,
    forming a pivot hole in the first metallic jaw member while the first and second metallic jaw members are held in the required orientation,
    forming a pivot hole in the second metallic jaw member while the first and second metallic jaw members are held in the required orientation, and
    inserting a pivot pin through the pivot hole in the first and second metallic jaw members to assemble the first and second metallic jaw members into a pair of jaws.

2. A method according to claim 1, wherein the required orientation is such that the planar sealing surface of the first metallic jaw member is parallel to the planar sealing surface of the second metallic jaw member.

3. A method according to claim 1, wherein the pivot hole is formed in the first and second metallic jaw members in a single operation.

4. A method according to claim 3, wherein the step of forming the pivot hole comprises drilling through the first and second metallic jaw members with a drill bit.

5. A method according to claim 1, including the initial steps of forming an initial hole in the first and second metallic jaw members before the assembly step, and filling the holes with a softer material before assembling the first and second metallic jaw members.

6. A method according to claim 5, wherein the softer material is a polymeric material.

7. A method according to claim 5, wherein the step of forming the pivot hole in the second metallic jaw member while the first and second jaw members are held in the required orientation comprises forming the pivot hole through the softer material after the holes have been filled with the softer material.

8. A method according to claim 7, wherein the diameter of the pivot hole in the second metallic jaw member is less than the diameter of the initial hole in each of the first and second metallic jaw members.

9. A method of manufacturing a pair of jaws for an electrosurgical instrument, comprising the steps of:

manufacturing first and second metallic jaw members, each metallic jaw member including a planar sealing surface, and an initial pivot hole, filling the initial pivot hole in each of the first and second metallic jaw members with a softer material, assembling the first and second metallic jaw members in a required orientation such that the planar sealing surface of the first metallic jaw member is at a predetermined orientation with respect to the sealing surface of the second metallic jaw member, holding the first and second metallic jaw members in the required orientation, forming a final pivot hole in the softer material of the first metallic jaw member while the first and second metallic jaw members are held in the required orientation and after the initial pivot hole in the first metallic jaw member has been filled with the softer material, forming a final pivot hole in the softer material of the second metallic jaw member while the first and second metallic jaw members are held in the required orientation and after the initial pivot hole in the second metallic jaw member has been filled with the softer material, and inserting a pivot pin through the final pivot holes in the first and second metallic jaw members to assemble the first and second metallic jaw members into a pair of jaws.

10. A method according to claim 9, wherein the diameter of the final pivot hole is less than the diameter of the initial pivot hole in each of the first and second metallic jaw members.

11. A method according to claim 9, wherein the softer material is a polymeric material.

* * * * *